US008053561B2

(12) United States Patent
Siekmann et al.

(10) Patent No.: US 8,053,561 B2
(45) Date of Patent: *Nov. 8, 2011

(54) PEGYLATED FACTOR VIII (75) Inventors: Juergen Siekmann, Vienna (AT); Katalin Varadi, Vienna (AT); Herbert Gritsch, Vienna (AT); Peter Turecek, Klosterneuburg (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 22 days.

This patent is subject to a terminal disclaimer.

(21) Appl. No.: 12/719,265

(22) Filed: Mar. 8, 2010

(65) Prior Publication Data

US 2010/0168391 A1 Jul. 1, 2010

Related U.S. Application Data (63) Continuation of application No. 11/729,625, filed on Mar. 29, 2007, now Pat. No. 7,683,158.

(60) Provisional application No. 60/787,968, filed on Mar. 31, 2006, provisional application No. 60/790,239, filed on Apr. 6, 2006.

(51) Int. Cl.
A61K 38/00 (2006.01)
A61K 38/37 (2006.01)
C07K 14/435 (2006.01)
C07K 14/755 (2006.01)

(52) U.S. Cl. ......... 530/383; 530/380; 530/381; 424/530

(58) Field of Classification Search .................. None
See application file for complete search history.

(56) References Cited

U.S. PATENT DOCUMENTS

| | | |
|---|---|---|
| 4,179,337 A | 12/1979 | Davis et al. |
| 4,356,170 A | 10/1982 | Jennings et al. |
| 4,757,006 A | 7/1988 | Toole, Jr. et al. |
| 4,877,608 A | 10/1989 | Lee et al. |
| 4,965,199 A | 10/1990 | Capon et al. |
| 4,970,300 A | 11/1990 | Fulton et al. |
| 5,122,614 A | 6/1992 | Zalipsky |
| 5,153,265 A | 10/1992 | Shadle et al. |
| 5,198,349 A | 3/1993 | Kaufman |
| 5,198,493 A | 3/1993 | Holmberg et al. |
| 5,250,421 A | 10/1993 | Kaufman et al. |
| 5,298,643 A | 3/1994 | Greenwald |
| 5,328,694 A | 7/1994 | Schwinn |
| 5,470,954 A | 11/1995 | Neslund et al. |
| 5,492,821 A | 2/1996 | Callstrom et al. |
| 5,539,063 A | 7/1996 | Hakimi et al. |
| 5,565,427 A | 10/1996 | Freudenberg |
| 5,605,884 A | 2/1997 | Lee et al. |
| 5,618,788 A | 4/1997 | Capon et al. |
| 5,621,039 A | 4/1997 | Hallahan et al. |
| 5,733,873 A | 3/1998 | Osterberg et al. |
| 5,846,951 A | 12/1998 | Gregoriadis |
| 5,919,766 A | 7/1999 | Osterberg et al. |
| 5,969,040 A | 10/1999 | Hallahan et al. |
| 6,005,077 A | 12/1999 | Schwarz et al. |
| 6,037,452 A | 3/2000 | Minamino et al. |
| 6,048,720 A | 4/2000 | Dalborg et al. |
| 6,183,738 B1 | 2/2001 | Clark |
| 6,379,933 B1 | 4/2002 | Johnson et al. |
| 6,455,639 B1 | 9/2002 | Yasukohchi et al. |
| 6,566,506 B2 | 5/2003 | Greenwald et al. |
| 6,586,398 B1 | 7/2003 | Kinstler et al. |
| 6,586,573 B1 | 7/2003 | Besman et al. |
| 6,692,931 B1 | 2/2004 | Reutter et al. |
| 6,743,908 B2 | 6/2004 | Filpula et al. |
| 6,806,063 B2 | 10/2004 | Pedersen et al. |
| 6,864,350 B2 | 3/2005 | Harris |
| 6,872,393 B2 | 3/2005 | Whitlow et al. |
| 6,913,915 B2 | 7/2005 | Ensor et al. |
| 7,118,737 B2 | 10/2006 | Kochendoerfer et al. |
| 7,199,223 B2 | 4/2007 | Bossard et al. |
| 7,230,081 B1 | 6/2007 | Jensen et al. |
| 7,338,788 B2 | 3/2008 | Pedersen et al. |
| 7,645,860 B2 | 1/2010 | Turecek et al. |
| 2003/0143596 A1 | 7/2003 | Bentley et al. |
| 2004/0132640 A1 | 7/2004 | DeFrees et al. |
| 2004/0247634 A1 | 12/2004 | Martinod et al. |
| 2005/0106658 A1 | 5/2005 | Defrees |
| 2006/0160948 A1 | 7/2006 | Scheiflinger et al. |

(Continued)

FOREIGN PATENT DOCUMENTS

EP 0306968 3/1989

(Continued)

OTHER PUBLICATIONS

Abuchowski et al., Cancer therapy with chemically modified enzymes. I. Antitumor properties of polyethylene glycol-asparaginase conjugates. *Cancer Biochem. Biophys.* 7: 175-86 (1984).

Avigad et al., The D-galactose oxidase of *Polyporus circinatus*, *J. Biol. Chem.*, 237:2736-43 (1962).

Baxter announces collaborations to develop longer acting forms of blood clotting factors, Baxter News (online), Sep. 29, 2005.

Bi et al., Targeted disruption of the mouse factor VIII gene produces a model of haemophilia A, *Nat. Genet.*, 10:119-21 (1995).

*Blood coagulation factor derivatives with side chain of amino acids moiety bound via coupling agent to poly:alkylene glycol* [abstract], Derwent, Sep. 29, 1984, (JP 01 742043, Nippon Chemiphar Co., Mar. 15, 1993).

(Continued)

*Primary Examiner* — Lisa J Hobbs (74) *Attorney, Agent, or Firm* — Marshall, Gerstein & Borun LLP (57) ABSTRACT

The invention is a proteinaceous construct comprising a Factor VIII molecule having at least a portion of the B domain intact, which is conjugated to a water-soluble polymer such as polyethylene glycol having a molecular weight of greater than 10,000 Daltons. The construct has a biological activity of at least 80% of the biological activity of native Factor VIII, and the in vivo half-life of the construct is increased by at least 1.5 fold as compared to the in vivo half-life of native factor FVIII.

21 Claims, 7 Drawing Sheets

U.S. PATENT DOCUMENTS

| | | | |
|---|---|---|---|
| 2006/0276634 A1 | 12/2006 | Nakamura et al. | |
| 2007/0244301 A1 | 10/2007 | Siekmann et al. | |
| 2009/0076237 A1 | 3/2009 | Turecek et al. | |

FOREIGN PATENT DOCUMENTS

| | | |
|---|---|---|
| EP | 0605963 | 7/1994 |
| EP | 0774261 | 5/1997 |
| EP | 0784632 | 7/1997 |
| EP | 0977584 | 2/2000 |
| EP | 1258497 | 11/2002 |
| EP | 1260582 | 11/2002 |
| WO | WO-86/06096 | 10/1986 |
| WO | WO-91/09122 | 6/1991 |
| WO | WO-92/16555 | 10/1992 |
| WO | WO-93/00357 | 1/1993 |
| WO | WO-94/05332 | 3/1994 |
| WO | WO-94/15625 | 7/1994 |
| WO | WO-94/15626 | 7/1994 |
| WO | WO-94/29370 | 12/1994 |
| WO | WO-96/40731 | 12/1996 |
| WO | WO-97/11957 | 4/1997 |
| WO | WO-97/19701 | 6/1997 |
| WO | WO-98/25969 A1 | 6/1998 |
| WO | WO-98/38219 A1 | 9/1998 |
| WO | WO-00/23114 | 4/2000 |
| WO | WO-00/48635 | 8/2000 |
| WO | WO-00/49047 A1 | 8/2000 |
| WO | WO-01/05434 | 1/2001 |
| WO | WO-01/37893 | 5/2001 |
| WO | WO-03/040211 | 5/2003 |
| WO | WO-2004/075923 | 9/2004 |
| WO | WO-2004/081053 | 9/2004 |
| WO | WO-2004/089280 | 10/2004 |
| WO | WO-2005/032581 | 4/2005 |
| WO | WO-2005/058366 | 6/2005 |
| WO | WO-2006/071801 | 7/2006 |
| WO | WO-2008/025856 | 3/2008 |
| WO | WO-2008/074032 | 6/2008 |

OTHER PUBLICATIONS

Brown et al., An ELISA test for the binding of von Willebrand antigen to collagen, *Thromb. Res.*, 43:303-11 (1986).

Caliceti et al., Pharmacokinetics of pegylated interferons: What is misleading? *Digest. Liver Dis.* 36(Suppl. 3): S334-9 (2004).

Denis et al., A mouse model of severe von Willebrand disease: defects in hemostasis and thrombosis, *Proc. Natl. Acad. Sci. USA*, 95:9524-9 (1998).

DeRomeuf et al., Heparin binding assay of von Willebrand factor (vWF) in plasma milieu—evidence of the importance of the multimerization degree of vWF, *Thromb. Haemost.*, 69:436-40 (1993).

Elodi et al., Kinetics of formation of factor IXa-factor VIII complex on the surface of platelets, *Thromb. Res.*, 21:695-700 (1981).

European Pharmacopoeia (Ph. Eur.) 3rd ed., 2.7.4 (1997).

European Search Report for corresponding European Application No. EP07754130.8, dated May 7, 2009.

Favaloro, Collagen binding assay for von Willebrand factor (VWF:CBA): detection of von Willebrands Disease (VWD), and discrimination of VWD subtypes, depends on collagen source, *Thromb. Haemost.*, 83:127-35 (2000).

Fernandes et al., Polysialylated asparaginase: preparation, activity and pharmacokinetics, *Biochim. Biophys. Acta*, 1341:26-34 (1997).

Final office action from U.S. Appl. No. 11/317,582, dated Aug. 18, 2009.

Fischer et al., Biochemical and functional characterization of recombinant von Willebrand factor produced on a large scale, *Cell Mol. Life Sci.*, 53:943-50 (1997).

Fischer et al., Structural analysis of recombinant von Willebrand factor produced at industrial scale fermentation of transformed CHO cells co-expressing recombinant furin, *FEBS Lett.*, 375:259-62 (1995).

Fischer et al., Structural analysis of recombinant von Willebrand factor: identification of hetero- and homo-dimers, *FEBS Lett.*, 351:345-8 (1994).

Girma et al., Structure-function relationship of the A1 domain of von Willebrand factor, *Thromb. Haemost.*, 74:156-60 (1995).

Gregoriadis et al., Polysialic acids: potential in drug delivery, *FEBS Lett.*, 315:271-276, 1993.

Gregoriadis et al., Polysialic acids: potential in improving the stability and pharmokinetics of proteins and other therapeutics, *CMLS Cell. Mol. Life Sci.*, 57:1964-1969 (2000).

Gregoriadis et al., Polysialylated proteins: an approach to improving enzyme stability and half-life in the blood circulation, *Sciences Techniques et Pratiques STP*, 9:61-66, 1999.

Harris et al., Effect of pegylation on pharmaceuticals. *Nat Rev. Drug Discovery.* 2: 214-21 (2003).

International Search Report and Written Opinion for International Application No. PCT/US2005/046879, mailed Jun. 19, 2007.

International Search Report and Written Opinion for corresponding International Application No. PCT/US2007/007560, mailed Sep. 18, 2007.

International Search Report and Written Opinion for International Application No. PCT/US09/52103, dated Feb. 25, 2010.

Jain et al., Polysialylated insulin: synthesis, characterization and biological activity in vivo, *Biochim. Biophys. Acta*, 1622:42-49 (2003).

Jain et al., Polysialylation: the natural way to improve the stability and pharmacokinetics of protein and peptide drugs, *Drug Delivery Systems & Sciences*, 4:3-9 (2004).

Jennings et al., Immunochemistry of groups A, B, and C meningococcal polysaccharide-tetanus toxoid conjugates, *J. Immunol.*, 127:1011-8 (1981).

Kaersgaard et al., Isolation of the factor VIII-von Willebrand factor complex directly from plasma by gel filtration, *J. Chromatogr. B Biomed. Sci. Appl.*, 715:357-67 (1998).

Kozlowski et al., Development of pegylated interferons for the treatment of chronic Hepatitis C. *BioDrugs.* 15(7): 419-29 (2001).

Lankhof et al., von Willebrand factor without the A2 domain is resistant to proteolysis, *Thromb. Haemost.*, 77:1008-13 (1997).

Lee et al., N-terminal site-specific mono-PEGylation of epidermal growth factor, *Pharm. Res.*, 20:818-25 (2003).

Lenting et al., An experimental model to study the in vivo survival of von Willebrand factor. Basic aspects and application to the R1205H mutation, *J. Biol. Chem.*, 279:12102-9 (2004).

Lewis et al., A facile, water-soluble method for modification of proteins with DOTA: use of elevated temperature and optimized pH to achieve high specific activity and high chelate stability in radiolabeled immunoconjugates, *Bioconj. Chem.*, 6:565-576 (1994).

Luo et al., A hyaluronic acid-taxol antitumor bioconjugate targeted to cancer cells [abstract], Biomacromolecules, 1:208-218 (2000).

Luo et al., Synthesis and selective cytotoxicity of a hyaluronic acid-antitumorbioconjugate [abstract], Bioconj. Chem., 10:755-763 (1999).

MacFarlane et al., Letter: A method for assaying von Willebrand factor (ristocetin cofactor), *Thromb. Diath. Haemorrh.*, 34:306-8 (1975).

Migneault et al., Glutaraldehyde: behavior in aqueous solution, reaction with proteins, and application to enzyme crosslinking, *BioTechniques*, 37:790-6, 798-802 (2004).

Nektar Advanced PEGylation Catalog 2005-2006, p. 30 (2005).

Nektar Advanced PEGylation Price List 2005-2006, p. 11 (2005).

NOF Corporation DDS Catalogue, p. 58 (2005).

Nonfinal office action from U.S. Appl. No. 11/317,582, dated Dec. 24, 2008.

Nonfinal office action from U.S. Appl. No. 12/184,567, dated Dec. 29, 2008.

Pietu et al., Production in *Escherichia coli* of a biologically active subfragment of von Willebrand factor corresponding to the platelet glycoprotein lb, collagen and heparin binding domains, *Biochem. Biophys. Res. Commun.*, 164:1339-47 (1989).

Roberts et a., Chemistry for peptide and protein pegylation *Adv. Drug Del. Rev.* 54: 459-76 (2002).

Rosen et al., Assay of factor VIII: C with a chromogenic substrate. *Scand J. Haematol.* 33(Suppl. 40): 139-45 (1984).

Rostin et al., B-domain deleted recombinant coagulation factor VIII modified with monomethoxy polyethylene glycol. *Bioconjugate Chem.* 11:387-96 (2000).

Roussi et al., Effects of human recombinant, plasma-derived and porcine von Willebrand factor in pigs with severe von Willebrand disease, *Blood Coagul. Fibrinolysis*, 9:361-72 (1998).

Ruggeri et al., The complex multimeric composition of factor VIII/von Willebrand factor, *Blood*, 57:1140-3 (1981).

Ruggeri, Structure and function of von Willebrand factor, *Thromb. Haemost.*, 82:576-84 (1999).

Saenko et al., Strategies towards a longer acting factor VIII, *Haemophilia*, 12:42-51 (2006).

Sakuragawa et al., Studies on the stability of factor VIII modified by polyethylene glycol, *Acta Medica Biologica*, 36:1-5 (1988).

Schlokat et al., Production of highly homogeneous and structurally intact recombinant von Willebrand factor multimers by furin-mediated propeptide removal in vitro, *Biotechnol. Appl. Biochem.*, 24:257-67 (1996).

Schwarz et al., Evaluation of recombinant von Willebrand factor in a canine model of von Willebrand disease, *Haemophilia*, 4:53-62 (1998).

Schwarz et al., Recombinant von Willebrand factor—insight into structure and function through infusion studies in animals with severe von Willebrand disease, *Semin. Thromb. Hemost.*, 28:215-26 (2002).

Seffernick et al., Melamine deaminase and atrazine chlorohydrolase: 98% identical but functionally different. *J. Bacteriology*. 2405-10 (2001).

Severs et al., Characterization of PEGylated factor VIII molecules, *Blood*, 108:11-12 (2006).

Study shows molecular size and structure of PEG interferon molecules, as used in pegintron(R), affect antiviral activity in vitro. *Hispanic PR Wire*, Oct. 28, 2003.

Tsubery et al., Prolonging the action of protein and peptide drugs by a novel approach of reversible polyethylene glycol modification. *J. Biol. Chem.* 279(37): 38118-24 (2004).

Tsusumi et al., Site-specific chemical modification with polyethylene glycol of recombinant immunotoxin anti-Tac(Fv)-PE38 (LMB-2) improves antitumor activity and reduces animal toxicity and immunogenicity. *Proc. Natl. Acad. Sci. USA*. 97:8548-53 (2000).

Turecek et al., Comparative study on collagen-binding enzyme-linked immunosorbent assay and ristocetin cofactor activity assays for detection of functional activity of von Willebrand factor, *Semin. Thromb. Hemost.*, 28:149-60 (2002).

Turecek et al., In vivo characterization of recombinant von Willebrand factor in dogs with von Willebrand disease, *Blood*, 90:3555-67 (1997).

Turecek et al., Modification of rVWF with polysialic acid: biochemical and functional characterization in mice with VWD, *Blood*, 108:298A-299A (2006).

Turecek et al., PDG modified rVFW prolongs the survival of native rFVIII in hemophilia A knock-out mice, *Blood*, 108:299A (2006).

Urrutigoity et al., Biocatalysis in organic solvents with a polymer-bound horseradish peroxidase. *Biocatalysis*. 2: 145-9 (1989).

Veronese et al., Bioconjugation in pharmaceutical chemistry. *IL Farmaco*. 54: 497-516 (1999).

Weiss et al., Quantitative assay of a plasma factor deficient in von Willebrand's disease that is necessary for platelet aggregation. Relationship to factor VIII procoagulant activity and antigen content, *J. Clin. Invest.*, 52:2708-16 (1973).

Wells et al., Additivity of mutational effects in proteins. *Biochemistry*. 29(37): 8509-17 (1990).

Wilchek et al., Labeling glycoconjugates with hydrazide reagents. *Methods Enzymol*. 138: 429-42 (1987).

Zalipsky et al., Hydrazide derivatives of poly (ethylene glycol) and their bioconjugates. *Poly(ethylene glycol) Chemistry and Biological Applications*. Chapter 21, pp. 318-341 (1997).

PEGYLATED FACTOR VIII

CROSS-REFERENCE TO RELATED APPLICATIONS

This application is a continuation of U.S. Ser. No. 11/729,625 filed Mar. 29, 2007, which claims the priority of U.S. Ser. No. 60/787,968 filed Mar. 31, 2006, and U.S. Ser. No. 60/790,239 filed Apr. 6, 2006, the entire respective disclosures of which are incorporated herein by reference.

FIELD OF THE INVENTION

The present invention relates to a proteinaceous construct comprising coagulation factor VIII (FVIII) being bound to at least one soluble polymer, such as a poly(alkylene oxide) such as polyethylene glycol. Further the present invention relates to methods for prolonging the in vivo-half-life of FVIII in the blood of a mammal having a bleeding disorder associated with functional defects or deficiencies of FVIII.

BACKGROUND OF THE INVENTION

Coagulation factor VIII (FVIII) circulates in plasma at a very low concentration and is bound non-covalently to von Willebrand factor (VWF). During hemostasis, FVIII is separated from VWF and acts as a cofactor for activated factor IX (FIXa)-mediated factor X (FX) activation by enhancing the rate of activation in the presence of calcium and phospholipids or cellular membranes.

FVIII is synthesized as a single-chain precursor of approximately 270-330 kD with the domain structure A1-A2-B-A3-C1-C2. When purified from plasma, FVIII is composed of a heavy chain (A1-A2-B) and a light chain (A3-C1-C2). The molecular mass of the light chain is 80 kD whereas, due to proteolysis within the B domain, the heavy chain is in the range of 90-220 kD.

FVIII is also synthesized as a recombinant protein for therapeutic use in bleeding disorders. Various in vitro assays have been devised to determine the potential efficacy of recombinant FVIII (rFVIII) as a therapeutic medicine. These assays mimic the in vivo effects of endogenous FVIII. In vitro thrombin treatment of FVIII results in a rapid increase and subsequent decrease in its procoagulant activity, as measured by in vitro assay. This activation and inactivation coincides with specific limited proteolysis both in the heavy and the light chains, which alter the availability of different binding epitopes in FVIII, e.g. allowing FVIII to dissociate from VWF and bind to a phospholipid surface or altering the binding ability to certain monoclonal antibodies.

The lack or dysfunction of FVIII is associated with the most frequent bleeding disorder, hemophilia A. The treatment of choice for the management of hemophilia A is replacement therapy with plasma derived or rFVIII concentrates. Patients with severe haemophilia A with FVIII levels below 1%, are generally on prophylactic therapy with the aim of keeping FVIII above 1% between doses. Taking into account the average half-lives of the various FVIII products in the circulation, this can usually be achieved by giving FVIII two to three times a week.

There are many concentrates on the market for the treatment of hemophilia A. One of these concentrates is the recombinant product Advate®, which is produced in CHO-cells and manufactured by Baxter Healthcare Corporation. No human or animal plasma proteins or albumin are added in the cell culture process, purification, or final formulation of this product.

The aim of many manufacturers of FVIII concentrates and therapeutic polypeptide drugs is to develop a next generation product with enhanced pharmacodynamic and pharmacokinetic properties, while maintaining all other product characteristics.

Therapeutic polypeptide drugs are rapidly degraded by proteolytic enzymes and neutralized by antibodies. This reduces their half-life and circulation time, thereby limiting their therapeutic effectiveness. The addition of a soluble polymer or carbohydrate to a polypeptide has been shown to prevent degradation and increase the polypeptides half-life. For instance, PEGylation of polypeptide drugs protects them and improves their pharmacodynamic and pharmacokinetic profiles (Harris J M et Chess R B, Nat Rev Drug Discov 2003; 2:214-21). The PEGylation process attaches repeating units of polyethylene glycol (PEG) to a polypeptide drug. PEGylation of molecules can lead to increased resistance of drugs to enzymatic degradation, increased half-life in vivo, reduced dosing frequency, decreased immunogenicity, increased physical and thermal stability, increased solubility, increased liquid stability, and reduced aggregation.

Thus, the addition of a soluble polymer, such as through PEGylation is one approach to improve the properties of a FVIII product. The state of the art is documented by different patents and patent applications:

U.S. Pat. No. 6,037,452 describes a poly(alkylene oxide)-FVIII or FIX conjugate, where the protein is covalently bound to a poly(alkylene oxide) through carbonyl-groups of said FVIII.

EP1258497B1 describes a method to prepare conjugates of FVIII and a biocompatible polymer. This patent was supplemented by a publication of Röstin et al. (Bioconj Chem 2000; 11:387-96). The conjugates comprise a B-domain deleted recombinant FVIII modified with monomethoxy polyethylene glycol. The conjugate had reduced FVIII function and the coagulant activity decreased rapidly with the degree of modification.

WO04075923A3 describes polymer-FVIII molecular conjugate comprising a plurality of conjugates wherein each conjugate has one to three water soluble polymers covalently attached to an FVIII molecule. The FVIII molecule is B-domain-deleted.

U.S. Pat. No. 4,970,300 describes a modified FVIII, wherein an infusible conjugate comprising a protein having FVIII activity was covalently linked to a nonantigenic ligand.

U.S. Pat. No. 6,048,720 describes conjugates of a polypeptide and a biocompatible polymer.

WO94/15625 describes FVIII bound to polyethylene glycol having a preferred molecular weight of no greater than 5,000 Daltons.

There remains a need for an FVIII having an attached soluble polymer to extend the half-life of the FVIII in vivo, for example, a PEGylated FVIII, such as full-length FVIII having PEG greater than 10,000 Daltons conjugated thereto, which retains functional activity while providing an extended half-life in vivo, as compared to non-PEGylated FVIII.

DETAILED DESCRIPTION OF THE INVENTION

The invention is a proteinaceous construct comprising an FVIII molecule having at least a portion of the B domain intact, bound to a water-soluble polymer which is a polyalkylene oxide, polyvinyl pyrrolidone, polyvinyl alcohol, polyoxazoline, a poly acryloylmorpholine or a carbohydrate, such as polysialic acid (PSA). In one embodiment of the invention, the water soluble polymer is a polyethylene glycol molecule having a molecular weight of greater than 10,000 Daltons. The construct retains the full functional activity of standard therapeutic FVIII products, and provides an extended half-life in vivo, as compared to standard therapeutic FVIII products.

The starting material of the present invention is FVIII, which can be derived from human plasma, or produced by recombinant engineering techniques, as described in patents U.S. Pat. Nos. 4,757,006; 5,733,873; 5,198,349; 5,250,421; 5,919,766; EP 306 968.

Herein, the term "Factor VIII" or "FVIII" refers to any FVIII molecule which has at least a portion of the B domain intact, and which exhibits biological activity that is associated with native FVIII. In one embodiment of the invention, the FVIII molecule is full-length Factor VIII. The FVIII molecule is a protein which is encoded for by DNA sequences capable of hybridizing to DNA encoding Factor VIII:C. Such a protein may contain amino acid deletions at various sites between or within the domains A1-A2-B-A3-C1-C2 (U.S. Pat. No. 4,868,112). The FVIII molecule may also be an analog of native FVIII wherein one or more amino acid residues have been replaced by site-directed mutagenesis.

By example, an FVIII molecule can be PEGylated by a variety of chemical methods (Roberts J M et al., Advan Drug Delivery Rev 2002; 54:459-76). For example, FVIII can be PEGylated by the conjugation of PEG to free SH groups using maleimide chemistry or the coupling of PEG hydrazides or PEG amines to carbohydrate moieties of the FVIII after prior oxidation.

In one embodiment of the invention, FVIII was modified via lysine residues by use of polyethylene glycol derivatives containing an active N-hydroxysuccinimide ester (NHS) such as Succinimidyl succinate, Succinimidyl glutarate or Succinimidyl propionate. These derivatives react with the lysine residues of FVIII under mild conditions by forming a stable amide bond. In one embodiment of the invention, the chain length of the PEG derivative is 5,000 Da. Other PEG derivatives with chain lengths of 500 to 2,000 Da, 2,000 to 5,000 Da, greater than 5,000 up to 10,000 Da or greater than 10,000 up to 20,000 Da, or greater than 20,000 up to 150,000 Da can be used, including linear and branched structures.

Alternative methods for the PEGylation of amino groups are the chemical conjugation with PEG carbonates by forming urethane bonds, or the reaction with aldehydes or ketones by reductive amination forming secondary amide bonds.

In the present invention an FVIII molecule is chemically modified using PEG derivatives that are commercially available. These PEG derivatives can have a linear or branched structures. Examples of PEG-derivatives containing NHS groups are listed below.

The following PEG derivatives are examples of those commercially available from Nektar Therapeutics (Huntsville, Ala.; see www.nektar.com/PEG reagent catalog; Nektar Advanced PEGylation, price list 2005-2006):

mPEG-Succinimidyl propionate (mPEG-SPA)

mPEG-Succinimidyl α-methylbutanoate (mPEG-SMB)

mPEG-CM-HBA-NHS (CM = carboxymethyl; HBA = Hydroxy butyric acid)

Structure of a Branched PEG-Derivative (Nektar Therapeutics):

Branched PEG N-Hydroxysuccinimide (mPEG2-NHS)

This reagent with branched structure is described in more detail by Kozlowski et al. (BioDrugs 2001; 5:419-29).

Other examples of PEG derivatives are commercially available from NOF Corporation (Tokyo, Japan; see www.nof.co.jp/english: Catalogue 2005)

General Structure of Linear PEG—Derivatives (NOF Corp.):

Structures of Branched PEG-Derivatives (NOF Corp.):

These propane derivatives show a glycerol backbone with a 1,2 substitution pattern. In the present invention branched PEG derivatives based on glycerol structures with 1,3 substitution or other branched structures described in US2003/0143596A1 can also be used.

PEG derivatives with degradable (for example, hydrolysable linkers) as described by Tsubery et al. (J Biol Chem 2004; 279:38118-24) and Shechter et al. (WO04089280A3) can also be used in the present invention.

Surprisingly, the PEGylated FVIII of this invention exhibits full functional activity, combined with an extended FVIII half-life in vivo. In addition the PEGylated rFVIII seems to be more resistant against thrombin inactivation. This was shown by a variety of in vitro and in vivo methods, and is illustrated by the following examples.

EXAMPLES

Example 1

PEGylation of Lysine Residues in rFVIII with mPEG Succinimidyl Succinate

A solution of a rFVIII bulk derived from the Advate manufacturing process (3,400 U/ml) was gel filtrated by use of Econo-Pac 10DG columns (Bio-Rad) using 20 mM Hepes buffer, 150 mM NaCl, pH 7.4, containing 0.5% sucrose and 0.1% Polysorbate 80. Then mPEG Succinimidyl succinate (Abuchowski et al. Cancer Biochim Biophys 1984; 7:175-86) with a chain length of 5,000 Da (PEG-SS 5000) was added to this solution under gentle stirring (5 mg PEG-SS/mg protein) and the pH value was adjusted to 7.4 by drop wise addition of 0.5 M NaOH. Then the PEGylation was carried out under gentle stirring for 1 hour at room temperature.

Subsequently the reaction mixture was applied onto an equilibrated ion-exchange chromatography resin (Fractogel EMD TMAE 650M/Pharmacia XK-10 column, bed height: 15.0 cm) in 20 mM Hepes buffer, 150 mM NaCl, pH 7.4, containing 0.5% sucrose and 0.1% Polysorbate 80. Then the column was washed with 20 CV equilibration buffer to remove excess reagent and the PEGylated rFVIII was eluted with elution buffer (20 mM Hepes, 1.0 M NaCl, 0.5% sucrose, 0.1% Polysorbate 80, pH 7.4). The eluate was concentrated by ultrafiltration/diafiltration with a membrane consisting of regenerated cellulose and with a molecular weight cut-off of 30 kD using a buffer system consisting of 20 mM Hepes, 150 mM NaCl, 0.5% sucrose, pH 7.4.

Example 2

Biochemical Characterization of PEGylated rFVIII in Vitro

RFVIII derived from the Advate manufacturing process was PEGylated according to Example 1 and the PEGylated FVIII product was biochemically characterized. The functional activity of the PEG-rFVIII was determined by use of the FVIII chromogenic assay (Rosen S, Scand J Haematol 1984; 33 (Suppl 40):139-45). The method is based on Ph. Eur. 5th edition (5.05) 2.7.4 Assay of Blood Coagulation Factor VIII.

A sample, containing factor VIII (FVIII:C) is mixed with thrombin, activated factor IX (FIXa), phospholipids and factor X (FX) in a buffer containing calcium. FVIII is activated by thrombin and subsequently forms a complex with phospholipids, FIXa and calcium ions. This complex activates factor X to factor Xa, which in turn cleaves the chromogenic substrate FXa-1 (AcOH*CH3OCO-D-CHA-Gly-Arg-pNA). The time course of para-nitroaniline (pNA) released is measured with a micro plate reader at 405 nm. The slope of the reaction is proportional to the factor VIII concentration in the sample. The FVIII antigen value was measured by use of an ELISA system commercially available (Cedarlane, Hornby, Ontario, Canada) with minor modifications. From these values the ratios FVIII chromogen/FVIII antigen were calculated. The protein content in the preparations was determined by measuring the optical density at 280 nm. From these data the protein content was calculated (Hoyer L W in: Human Protein Data. Installments 1-6; Heberli Ed.; Wiley VCH, Weinheim, Germany, 1998) and expressed in mg/ml.

TABLE 1

|  | Native rFVIII | PEG-rFVIII PEG-SS 5K (5 mg per mg protein) |
|---|---|---|
| FVIII:Chr activity [U/ml] | 3,430 | 64 |
| FVIII:Ag [U/ml] | 4,067 | 81 |
| Ratio FVIII:Chr/FVIII:Ag | 0.84 | 0.79 |
| Recovery of biological activity (%) | 100 | 94 |

The data in Table 1 shows that in the PEGylated rFVIII preparation, the biological activity (expressed by the ratio FVIII chromogenic activity to FVIII antigen) is recovered to more than 90% in comparison to the biological activity of the native rFVIII (100%).

Example 3

Characterization of PEGylated rFVIII by SDS-PAGE and Immunoblotting Techniques

Figure 1:
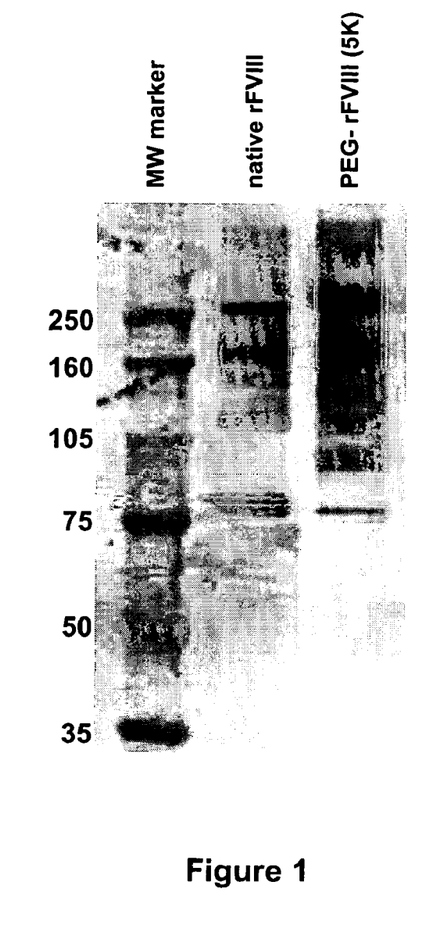
FIG. 1 shows the broadening and mass increase of rFVIII after conjugation with PEG measured by SDS-PAGE with subsequent immunoblotting.

Native rFVIII was characterized by SDS PAGE under reducing conditions by using a 4-12% polyacrylamide gradient gel obtained from Invitrogen (Carlsbad, Calif. USA) according to the instructions of the manufacturer. As molecular weight markers (MW) Precision Plus markers (10 kD-250 kD) obtained from Bio-Rad (Hercules, Calif., USA) were used. Then the proteins were transferred on a PVDF membrane obtained from Bio-Rad (Hercules, Calif., USA) by electroblotting and subsequently incubated with a polyclonal sheep anti human FVIII:C antibody obtained from Cedarlane (Hornby, Ontario, Canada). The last steps of the immunostaining procedure were the incubation with an alkaline phosphatase (ALP) conjugated anti-sheep antibody obtained from Accurate (Westbury, N.Y., USA) followed by the final visualization by use of an ALP substrate kit (Bio-Rad, Hercules, Calif., USA). The results are summarized in FIG. 1. The blot demonstrates the domain structure of native and PEGylated rFVIII. It is shown that the PEGylated rFVIII has broader bands and high molecular masses than the native recombinant protein.

Example 4

Pharmacokinetics of PEGylated rFVIII in a FVIII Deficient Knock Out Mouse Model

Figure 2:
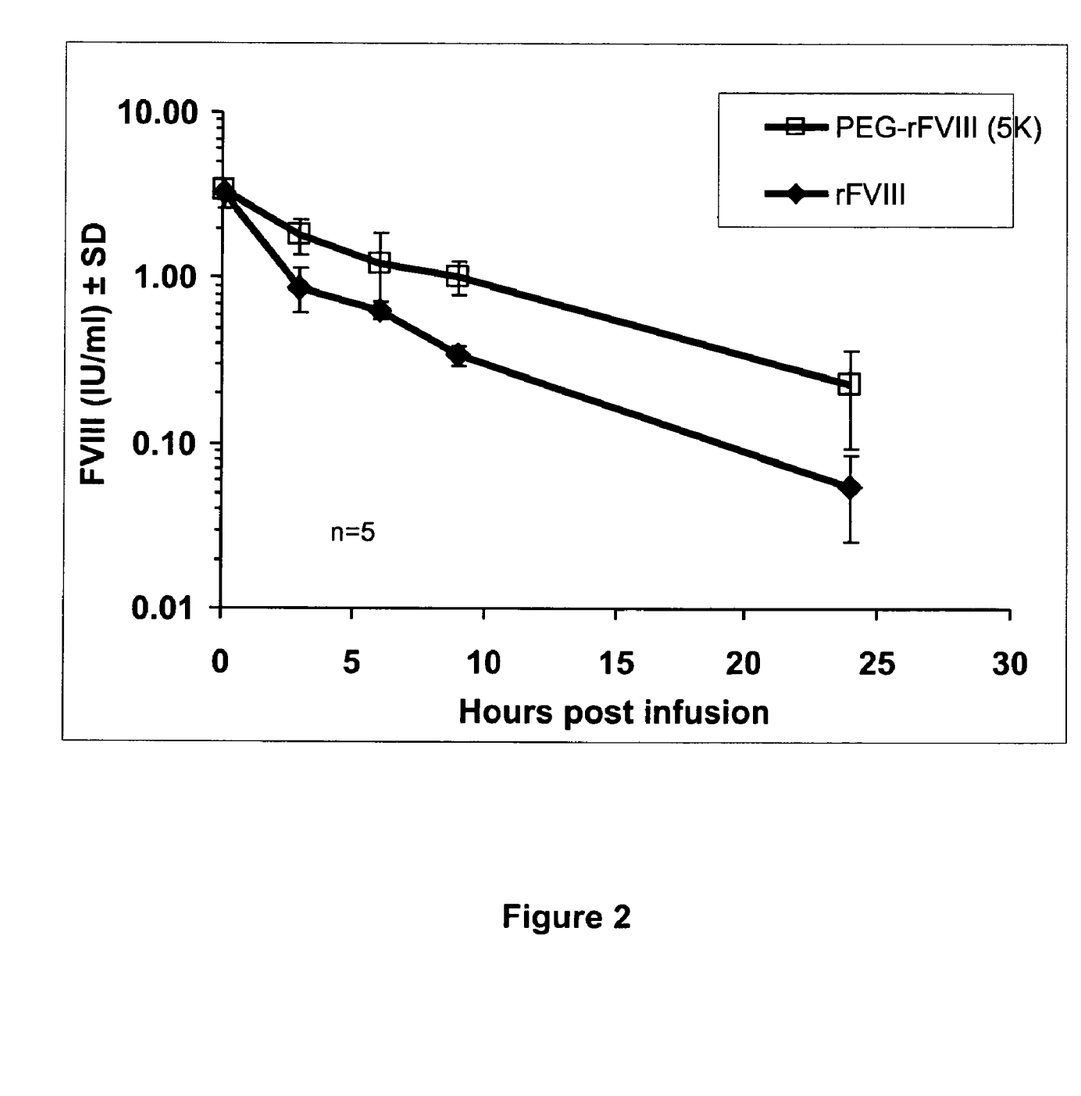
FIG. 2 shows the pharmacokinetics of PEG-rFVIII conjugate compared to non-conjugated FVIII in hemophilic mice. Open squares: PEGrFVIII, dose 200 IU FVIII/kg. Closed diamonds: native rFVIII, dose 200 IU FVIII/kg.

FVIII deficient mice described in detail by Bi et al. (Nat Genet 1995; 10:119-21) were used as a model of severe human hemophilia A. Groups of 5 mice received a bolus injection (10 ml/kg) via the tail vein with either PEG-rFVIII (PEG-SS, 5K) prepared according to Example 1 or native rFVIII in a dose of 200 IU FVIII/kg bodyweight. Citrate plasma by heart puncture after anesthesia was prepared from the respective groups, 5 minutes, 3, 6, 9 and 24 hours after injection. FVIII activity levels were measured in plasma samples. The results of this experiment are summarized in FIG. 2. Mean half life increased from 1.9 hours (for native rFVIII) to 4.9 hours (for PEGylated rFVIII), area under curve (AUC) increased from 13.0 to 25.2 hours*IU/ml. Half-life calculation was performed with MicroMath Scientist, model 1 from pharmacokinetic library (MicroMath, Saint Louis, Mo., USA).

Example 5

Detailed Analysis of PEGylation of rFVIII by SDS-PAGE and Immunoblotting Techniques Native and PEGylated rFVIII was digested with 1 nM thrombin for 60 minutes at 60° C., which resulted in specific cleavage of the FVIII molecule with well defined degradation products. These heavy- and light chain fragments were separated by SDS-PAGE followed by electroblotting, as described in Example 3. To visualize the cleaved fragments, a polyclonal antibody and monoclonal antibodies against the heavy chain A1 and A2 domains, the B domain and the light chain N-terminal A3 domain were applied.

Figure 3:
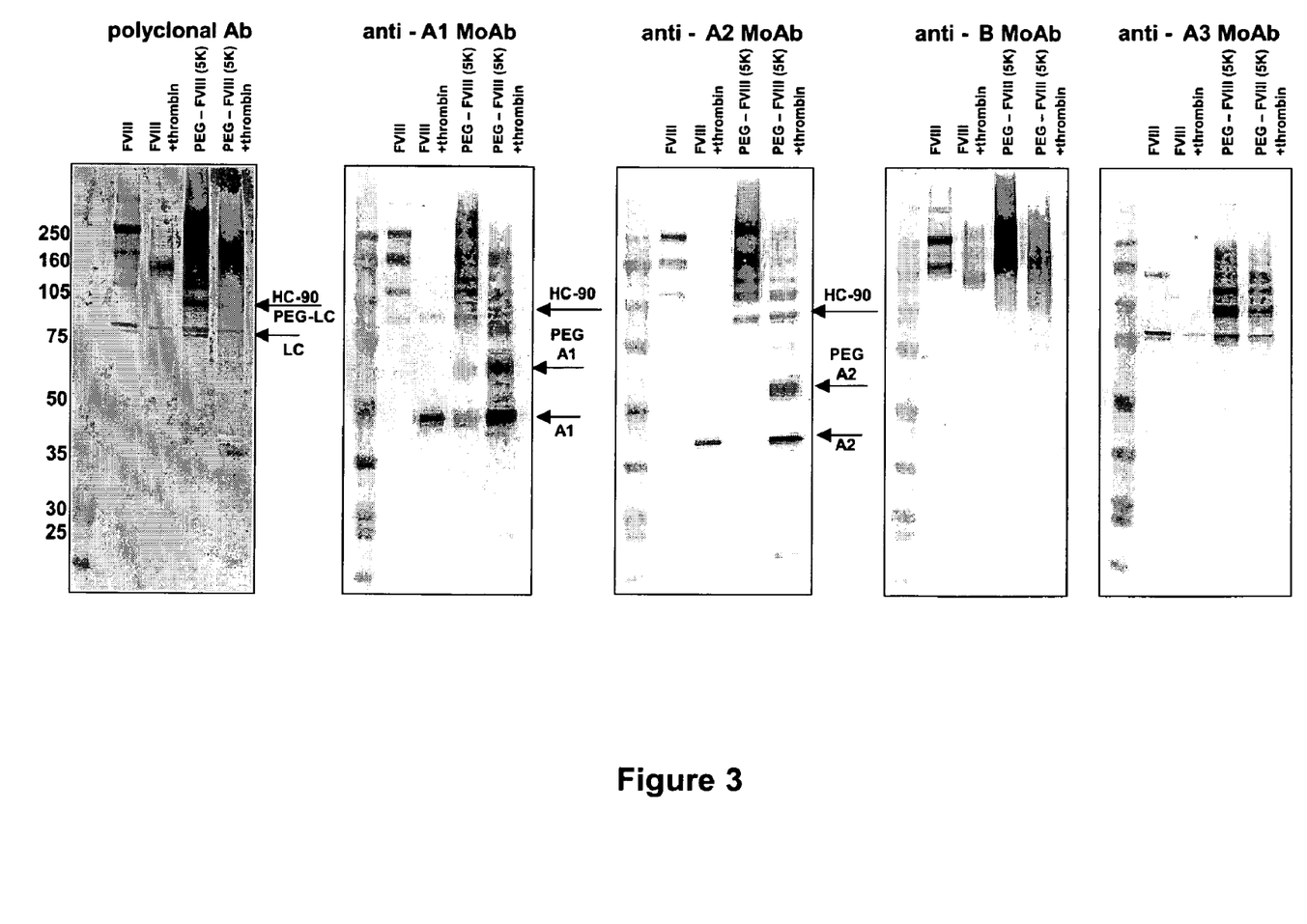
FIG. 3 shows the detailed analysis of PEGylation sites by SDS-PAGE using various anti FVIII antibodies.

As seen in FIG. 3 all domains were PEGylated, albeit to a different extent. The B domain was strongly PEGylated. Both the A1 and A2 domains of the heavy chain were partially PEGylated. Various PEGylation-degrees (mono-, di-, tri-...) could be observed in the light chain A3-domain. In agreement with Example 6, the PEGylated FVIII seemed to be more resistant to thrombin.

Example 6

Thrombin-Resistance of PEGylated rFVIII

In vitro thrombin treatment of FVIII results in a rapid increase and subsequent decrease in its procoagulant activity. The rate of activation and inactivation, which depends on the thrombin concentration and on the integrity of FVIII, was monitored by a FIXa cofactor assay, as follows:

FVIII was incubated at 37° C. with 0.5 or 1 nM thrombin. Subsamples were withdrawn at time intervals between 0.5 to 40 minutes and added to a mixture of FIXa, FX, PL-vesicles and $CaCl_2$ also containing a specific thrombin inhibitor to stop the further thrombin-mediated reactions and incubated for 3 minutes. A subsample was added to a chromogenic substrate, which is selectively cleaved by Fxa and contained EDTA to stop further Xa activation. After a 15 min incubation, the reaction was terminated by acetic acid. The absorbance (A405) values, which are proportional to the Fxa concentrations, were measured in an ELISA reader and converted to Fxa concentrations using a purified Fxa reference curve. The generated Fxa concentrations were plotted against the incubation time with thrombin.

Pseudo-first order inactivation rate of FVIII was determined by fitting the declining part of the curves with a single exponential fit.

TABLE 2

| Thrombin | First order inactivation Rate k' (1/min) | | Relative k' |
|---|---|---|---|
| | Native FVIII | PEG-FVIII | PEG/native |
| 0.5 nM | 0.14 | 0.08 | 0.57 |
| 1 nM | 0.24 | 0.14 | 0.58 |

Figure 4:
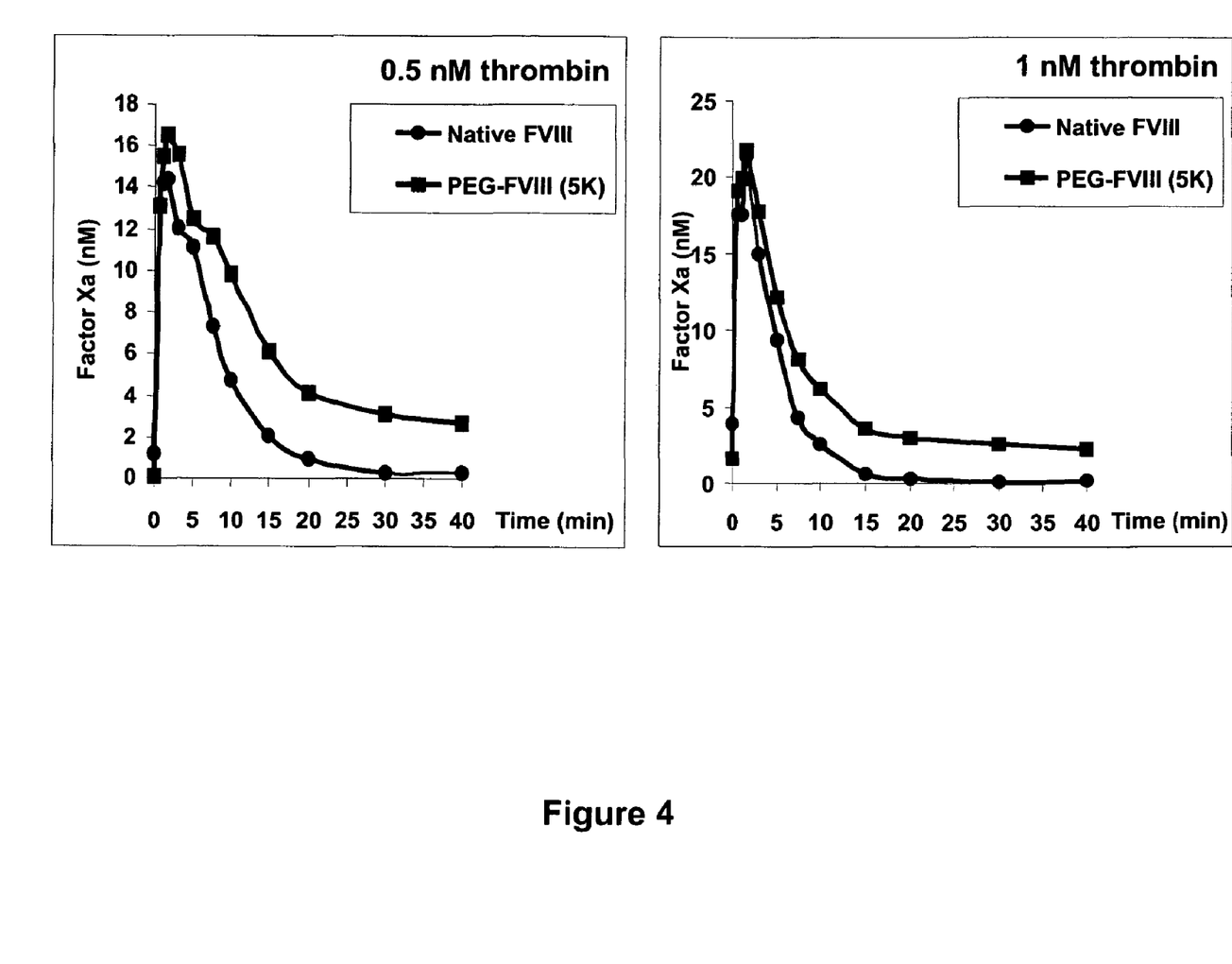
FIG. 4 shows the thrombin-induced activation and inactivation of native and PEGylated rFVIII.

As shown in FIG. 4 and Table 2, PEGylated rFVIII showed a slower inactivation rate at both applied thrombin concentrations.

Example 7

PEGylation of Lysine Residues in rFVIII with Branched 2,3-Bis(methylpolyoxyethylene-oxy)-1-(1,5-dioxo-5-succinimidyloxy, pentyloxy) propane A solution of rFVIII in 20 mM Hepes buffer pH 7.4 containing 150 mM NaCl, 0.5% sucrose and 0.1% Polysorbate 80 was prepared from bulk material derived from the Advate manufacturing process containing 489 IU FVIII/ml. A branched PEG succinimidyl glutarate (PEG-SG) reagent (2,3-Bis(methylpolyoxyethylene-oxy)-1-(1,5-dioxo-5-succinimidyloxy, pentyloxy)propane) obtained from NOF Corporation (Tokyo, Japan) with a molecular weight of 20 kD was added to 153 ml of this solution under gentle stirring (5 mg reagent/mg protein) and the pH value was adjusted to 7.4 by drop wise addition of 0.5 M NaOH after 10 minutes. Then the PEGylation of rFVIII was performed under gentle stirring for 1 hour at room temperature.

Subsequently the reaction mixture was applied onto an equilibrated ion-exchange chromatography resin (Fractogel EMD TMAE 650M/Pharmacia XK-50 column, bed height: 14.5 cm) in 20 mM Hepes buffer, 150 mM NaCl, pH 7.4, containing 0.5% sucrose and 0.1% Polysorbate 80 using a linear flow rate of 1 cm/min. The column was washed with 25 CV equilibration buffer to remove excess reagent (linear flow rate: 2 cm/min) and the PEGylated rFVIII was eluted with elution buffer (20 mM Hepes, 1.0 M NaCl, 0.5% sucrose, 0.1% Polysorbate 80, pH 7.4) at a linear flow rate of 0.5 cm/min. Then the eluate was concentrated by ultrafiltration/diafiltration with a membrane consisting of regenerated cellulose and with a molecular weight cut-off of 30 kD using a buffer system consisting of 20 mM Hepes, 150 mM NaCl, 0.5% sucrose, pH 7.4.

Example 8

In-Vitro Characterization of rFVIII PEGylated with Branched PEG-SG 20 kD

RFVIII derived from the Advate manufacturing process was PEGylated via lysine residues using a branched PEG-SG reagent according to Example 7 and the PEGylated rFVIII product was biochemically characterized as described in Example 2.

TABLE 3

| | Native rFVIII | PEG-rFVIII PEG-SG 20K (5 mg per mg protein) |
|---|---|---|
| FVIII:Chr activity [U/ml] | 9,950 | 1,040 |
| FVIII:Ag [U/ml] | 20,807 | 1,763 |
| Ratio FVIII:Chr/FVIII:Ag | 0.48 | 0.59 |
| Recovery of biological activity (%) | 100 | 120 |

The data in Table 3 show that in the PEGylated rFVIII preparation the biological activity (expressed by the ratio FVIII chromogenic activity to FVIII antigen) completely recovered in comparison to the biological activity of the native rFVIII (100%).

Figure 5:
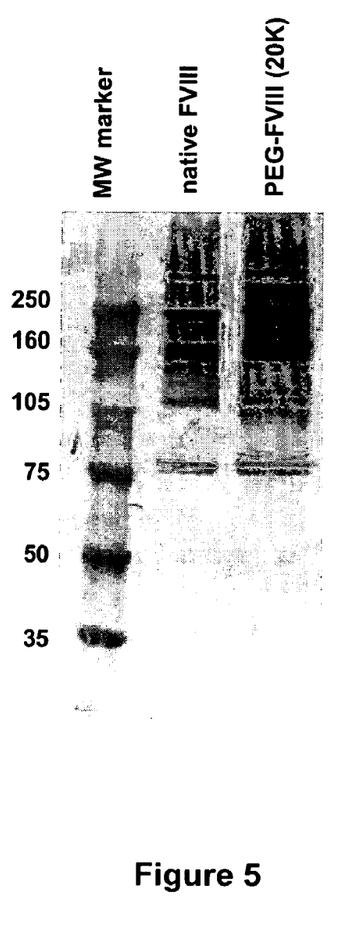
FIG. 5 shows the bands demonstrating the domains of native and PEGylated rFVIII.

The PEGylated rFVIII was characterized by SDS-PAGE and immunoblotting techniques under reducing conditions using a 4-12% polyacrylamide gradient gel as described in Example 3. The results are summarized in FIG. 5. The blot demonstrates the domain structure of native and PEGylated rFVIII. It is shown that the PEGylated rFVIII has broader bands and high molecular masses than the native recombinant protein.

Figure 6:
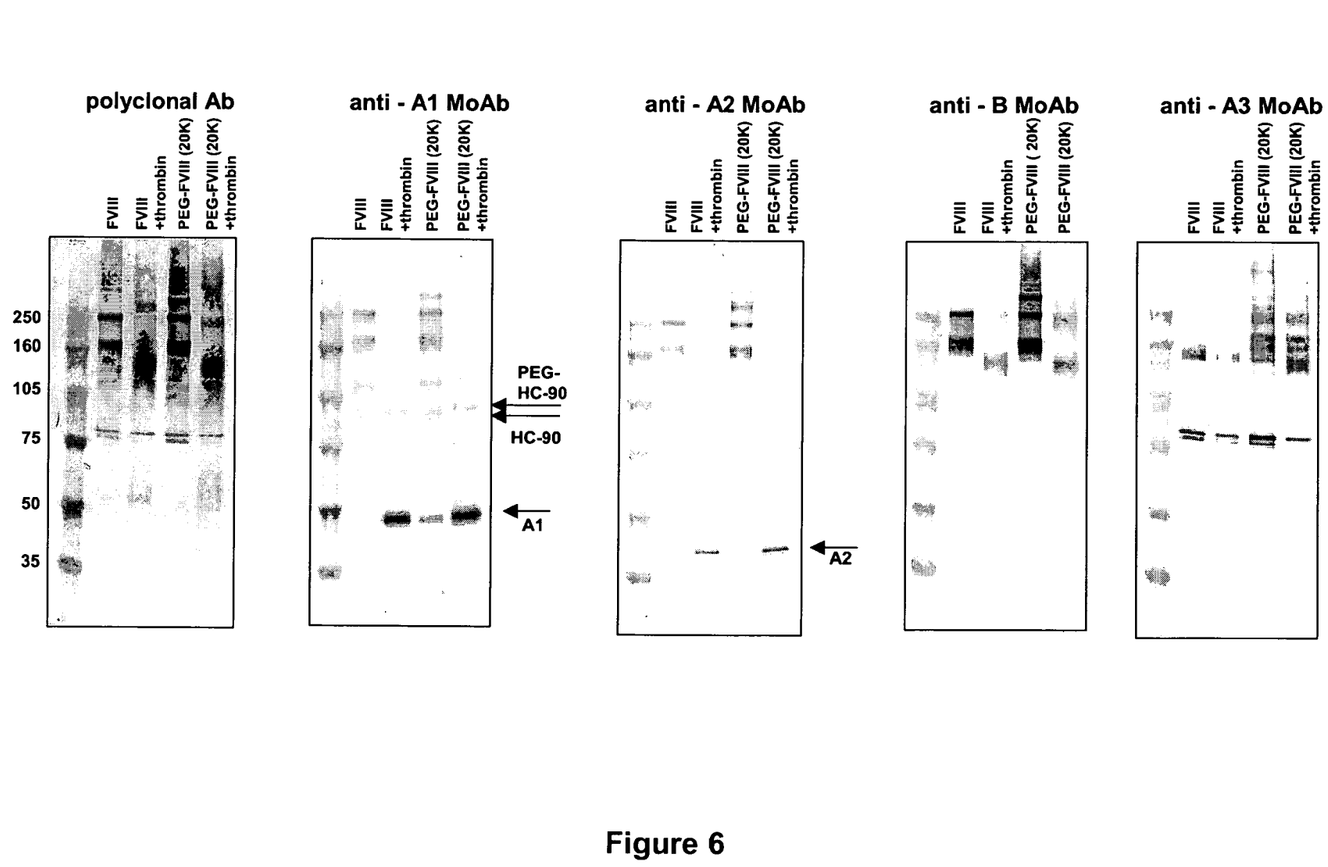
FIG. 6 shows the extent of PEGylation of various domains of native and PEGylated rFVIII.

For more detailed analysis of PEGylation of the rFVIII preparation by SDS-PAGE and immunoblotting techniques, the native and PEGylated rFVIII was digested with 1 nM thrombin for 60 minutes at 60°, which resulted in specific cleavage of the FVIII molecule with well defined degradation products, as described in Example 5. The fragments were separated by SDS-PAGE followed by electroblotting. and visualized by different anti-FVIII antibodies. As seen in FIG. 6, all domains were PEGylated, albeit to a different extent. The B domain was strongly PEGylated. Various PEGylation-degrees (mono-, di-, tri-PEGylation) could be observed in the light chain A3-domain. The results indicate that the PEGylated rFVIII seemed to be more resistant to thrombin.

The rate of activation and inactivation by thrombin was monitored by a FIXa cofactor assay as described in Example 6. Pseudo-first order inactivation rate of FVIII was determined by fitting the declining part of the curves with a single exponential fit.

TABLE 4

| Thrombin | First order inactivation Rate k' (1/min) | | Relative k' |
|---|---|---|---|
| | Native FVIII | PEG-FVIII | PEG/native |
| 0.5 nM | 0.13 | 0.09 | 0.67 |
| 1 nM | 0.21 | 0.15 | 0.71 |

Figure 7:
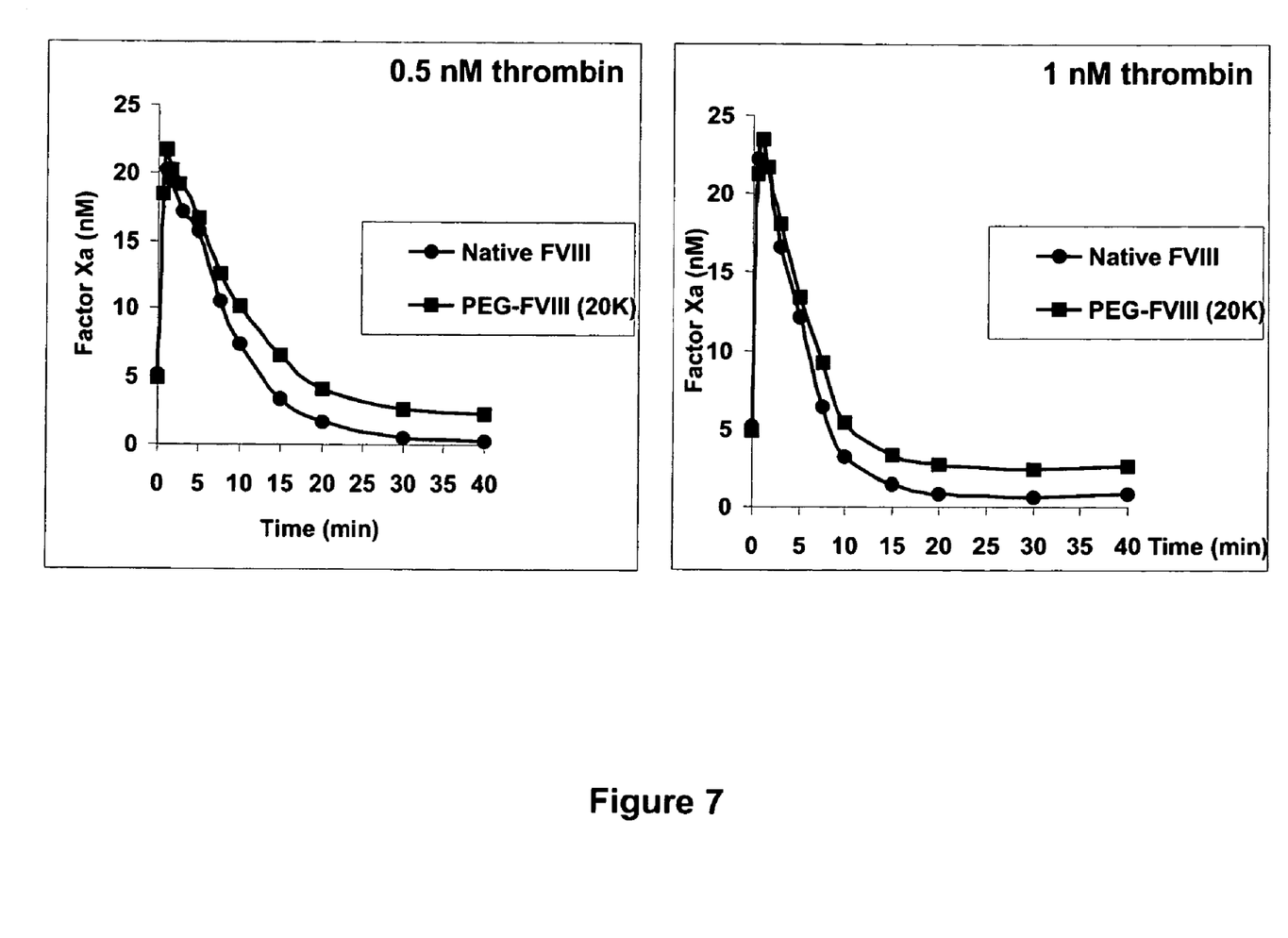
FIG. 7 shows the thrombin inactivation rate of native and PEGylated rFVIII.

As shown in FIG. 7 and Table 4, the PEGylated rFVIII showed a slower inactivation rate at both applied thrombin concentrations.

The invention claimed is:
1. A proteinaceous molecule having Factor VIII activity comprising, (a) a Factor VIII molecule; and (b) at least four polyethylene glycol molecules bound to said Factor VIII molecule, wherein three polyethylene glycol molecules are bound to said Factor VIII molecule in the A3 domain and at least one polyethylene glycol molecule is bound to said Factor VIII molecule in the B domain; said polyethylene glycol molecules having a molecular weight of greater than 10,000 Daltons; said proteinaceous molecule having a biological activity of at least 80% of the biological activity of native

Factor VIII, wherein the biological activities of the proteinaceous molecule and of native Factor VIII are determined by the ratios of chromogenic activity to Factor VIII antigen value (FVIII:Chr/FVIII:Ag), and wherein the in vivo half-life of said proteinaceous molecule is increased by at least 1.5 -fold as compared to the in vivo half-life of native Factor VIII.

2. The proteinaceous molecule of claim 1 wherein said Factor VIII molecule is a recombinant Factor VIII.

3. The proteinaceous molecule of claim 1 wherein said Factor VIII molecule is a plasma-derived Factor VIII.

4. The proteinaceous molecule of claim 1 wherein said Factor VIII molecule is full-length Factor VIII.

5. The proteinaceous molecule of claim 1 wherein said Factor VIII molecule has the B domain intact.

6. The proteinaceous molecule of claim 1 wherein said Factor VIII molecule has at least a portion of the B domain intact.

7. The proteinaceous molecule of claim 1 wherein said Factor VIII molecule is encoded by a DNA sequence capable of hybridizing to DNA encoding Factor VIII:C.

8. The proteinaceous molecule of claim 1 wherein said Factor VIII molecule has a heavy chain with a molecular weight of 90 to 220 kD.

9. The proteinaceous molecule of claim 1 wherein said polyethylene glycol molecules have a molecular weight of greater than 10,000 Da to about 125,000 Da.

10. The proteinaceous molecule of claim 1 wherein said polyethylene glycol molecules have a molecular weight of about 15,000 to about 20,000 Da.

11. The proteinaceous molecule of claim 1 wherein said polyethylene glycol molecules have a molecular weight of about 18,000 to about 25,000 Da.

12. The proteinaceous molecule of claim 1 wherein said polyethylene glycol molecules have a molecular weight of about 20,000 Da.

13. The proteinaceous molecule of claim 1 wherein said polyethylene glycol molecules have a molecular weight of about 20,000 to about 150,000 Da.

14. The proteinaceous molecule of claim 1 wherein said polyethylene glycol molecules have a linear or branched structure.

15. The proteinaceous molecule of claim 1 wherein said polyethylene glycol molecules have a degradable linker.

16. The proteinaceous molecule of claim 1 wherein said polyethylene glycol molecules have a hydrolysable linker.

17. The proteinaceous molecule of claim 1 wherein said polyethylene glycol molecules are bound to said Factor VIII molecule by conjugation of said polyethylene glycol molecules to a moiety selected from the group consisting of SH groups, carbohydrate moieties, and amino groups.

18. A composition comprising the proteinaceous molecule of claim 1, wherein said composition is substantially free from albumin.

19. A proteinaceous molecule having Factor VIII activity comprising, (a) a Factor VIII molecule; and (b) at least four soluble polymer or carbohydrate molecules bound to said Factor VIII molecule in the A1, A2 or A3 domain; said soluble polymer or carbohydrate molecules having a molecular weight of greater than 10,000 Daltons; said proteinaceous molecule having a biological activity of at least 80% of the biological activity of native Factor VIII, wherein the biological activities of the proteinaceous molecule and of native Factor VIII are determined by the ratios of chromogenic activity to Factor VIII antigen value (FVIII:Chr/FVIII:Ag), and wherein the in vivo half-life of said proteinaceous molecule is increased by at least 1.5-fold as compared to the in vivo half-life of native Factor VIII.

20. A proteinaceous molecule having Factor VIII activity comprising, (a) a Factor VIII molecule; and (b) at least four soluble polymer or carbohydrate molecules bound to said Factor VIII molecule, wherein three soluble polymer or carbohydrate molecules are bound to said Factor VIII molecule in the A1, A2 or A3 domain and at least one soluble polymer or carbohydrate molecule is bound to said Factor VIII molecule in the B domain; said soluble polymer or carbohydrate molecules having a molecular weight of greater than 10,000 Daltons; said proteinaceous molecule having a biological activity of at least 80% of the biological activity of native Factor VIII, wherein the biological activities of the proteinaceous molecule and of native Factor VIII are determined by the ratios of chromogenic activity to Factor VIII antigen value (FVIII:Chr/FVIII:Ag), and wherein the in vivo half-life of said proteinaceous molecule is increased by at least 1.5-fold as compared to the in vivo half-life of native Factor VIII.

21. A proteinaceous molecule having Factor VIII activity comprising, (a) a Factor VIII molecule; and (b) at least four soluble polymer or carbohydrate molecules bound to said Factor VIII molecule, wherein at least one soluble polymer or carbohydrate molecule is bound to said Factor VIII molecule in the B domain; said soluble polymer or carbohydrate molecules having a molecular weight of greater than 10,000 Daltons; said proteinaceous molecule having a biological activity of at least 80% of the biological activity of native Factor VIII, wherein the biological activities of the proteinaceous molecule and of native Factor VIII are determined by the ratios of chromogenic activity to Factor VIII antigen value (FVIII:Chr/FVIII:Ag), and wherein the in vivo half-life of said proteinaceous molecule is increased by at least 1.5-fold as compared to the in vivo half-life of native Factor VIII.

* * * * *